United States Patent [19]
Goebel et al.

[11] Patent Number: 4,769,023
[45] Date of Patent: Sep. 6, 1988

[54] DISPOSABLE DIAPER

[76] Inventors: Arthur J. Goebel; Brenda B. Goebel, both of 499 S.R. 434 Suite 1017, Altamonte Springs, Fla. 32714; James F. Brooke, Sr.; Betty L. Brooke, both of P.O. Box 1221, Hawthorne, Fla. 32640

[21] Appl. No.: 89,266

[22] Filed: Aug. 25, 1987

[51] Int. Cl.⁴ ............................................. A61F 13/16
[52] U.S. Cl. ................................................ 604/385 R
[58] Field of Search ............................ 604/385.1, 381

[56] References Cited

U.S. PATENT DOCUMENTS 4,230,113 10/1980 Mehta ............................. 604/381 X
4,675,015 6/1987 Brown .............................. 604/385.1

Primary Examiner—John D. Yasko
Attorney, Agent, or Firm—William M. Hobby

[57] ABSTRACT

A disposable diaper apparatus is provided for use on babies and is made of a layered flat absorbent material having a generally rectangular shape and first and second end portions and a center portion. The center portion has arcuate edges extending into the generally rectangular shape to provide a form fitting diaper having a pair of attaching tapes for holding the first and second end portions together. The improvement in the diaper includes, a removable perforated area in the first end portion along one edge thereof and positioned to fit over a navel area of a baby wearing the diaper so that the perforated area can be removed for young babies to help prevent umbilical infection in the baby.

5 Claims, 2 Drawing Sheets

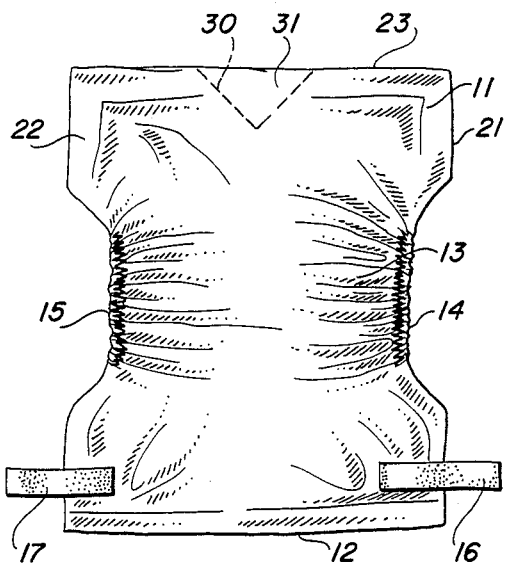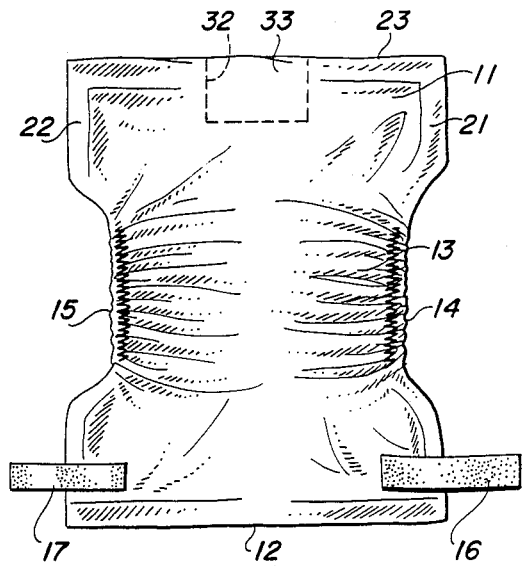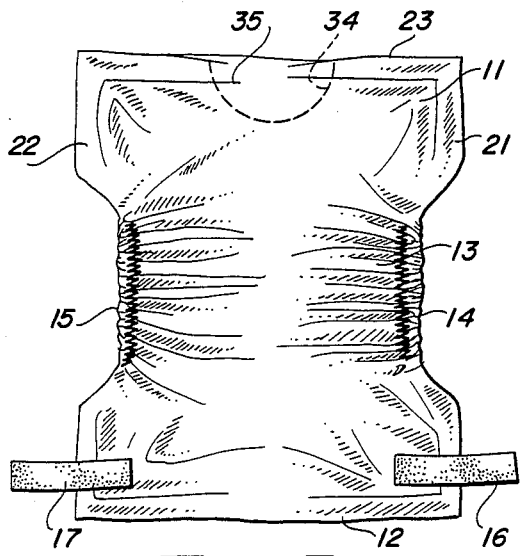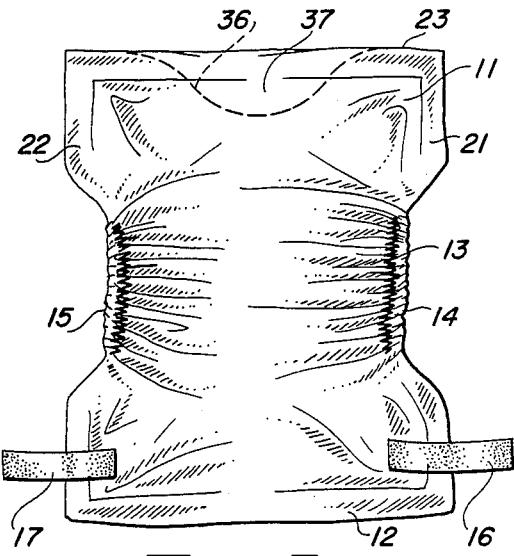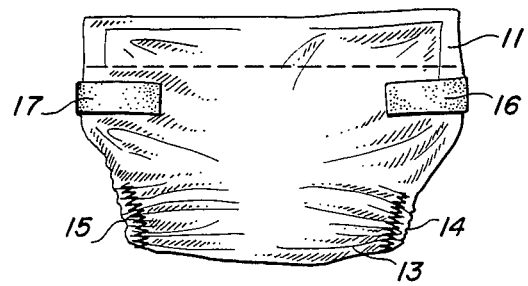

DISPOSABLE DIAPER

BACKGROUND OF THE INVENTION

The present invention relates to disposable diapers and especially to disposable diapers having a removable perforated area to keep the diaper off the umbilical area of newborn babies.

In the past a wide variety of baby diapers have been provided and have been made of absorbent material or cloth which can be folded to be wrapped around the baby prior to the baby being potty trained. Diapers were formerly held onto the baby with large safety pins. Disposable diapers or diapers made of absorbent cellulostic or other materials can be layered with absorbent material with increased thickness or absorbency in areas where increased absorbtion is needed. Disposable diapers generally have ready made attaching adhesive straps so that the diaper can be pulled from a box and strapped onto a baby. Once the diaper has been used, it can be taken off the thrown away and is biodegradable so that it can be disposed of through any conventional disposable means. Typical prior art baby diapers can be seen in the Mesmer U.S. Pat. No. 2,570,963 which is designed to avoid pricking the baby with pins and in the Hemple U.S. Pat. No. 91,334 having a lower than usual front on the diaper. The Kleinert U.S. Pat. No. 580,406, is for baby diapers as is the Ferris U.S. Pat. No. 631,629 and the Hughes U.S. Pat. No. 109,410, each of which patents show a diaper on a baby falling below the navel area of the baby.

The present invention is directed toward a disposable diaper having a perforated area which can be torn away for young babies to provide umbilicus relief from mechanical irritation and contact with urine or feces collected by the diaper to thereby prevent umbilical infection on a newborn baby prior to the healing of the umbilical area on the baby.

SUMMARY OF THE INVENTION

The present invention relates to disposable diapers and especially to disposable diapers for placing on a baby and made of a layered flat absorbent material having a generally rectangular shape having first and second end portions and a center portion. The center portion has arcuate edges extending into the generally rectangular shape to provide a form-fitting diaper. The diaper has a pair of attaching adhesive straps on the first or second ends for attaching the diaper to a baby. The improvement includes a removable perforated area in the first end portion along one edge thereof and positioned to fit over a navel area of a baby wearing the diaper, so that the perforated area can be removed for young babies to prevent umbilical infection in the baby. The first end portion of the diaper can have an end edge and two side edges with the removable perforated area positioned in the middle of the end edge to form a removed portion alongg the edge when the perforated portion is removed. The perforated portion can be of an arcuate shape of different sizes or maybe of a triangular or square shape as desired.

BRIEF DESCRIPTION OF THE DRAWINGS

Other objects, features and advantages of the present invention will be apparent from the written description and the drawings in which;

FIG. 3 is an elevational view of a second embodiment of a diaper in accordance with FIGS. 1 and 2;

FIG. 4 is an elevational view of another embodiment of a diaper in accordance with FIGS. 1 and 2;

FIG. 5 is an elevational view of another embodiment of the diaper of FIGS. 1 and 2;

FIG. 6 is an elevational view of another embodiment of a diaper of FIGS. 1 and 2; and FIG. 7 is a rear elevation of a diaper in accordance with the embodiments of FIGS. 1 and 2.

DESCRIPTION OF THE PREFERRED EMBODIMENT

Figure 1:
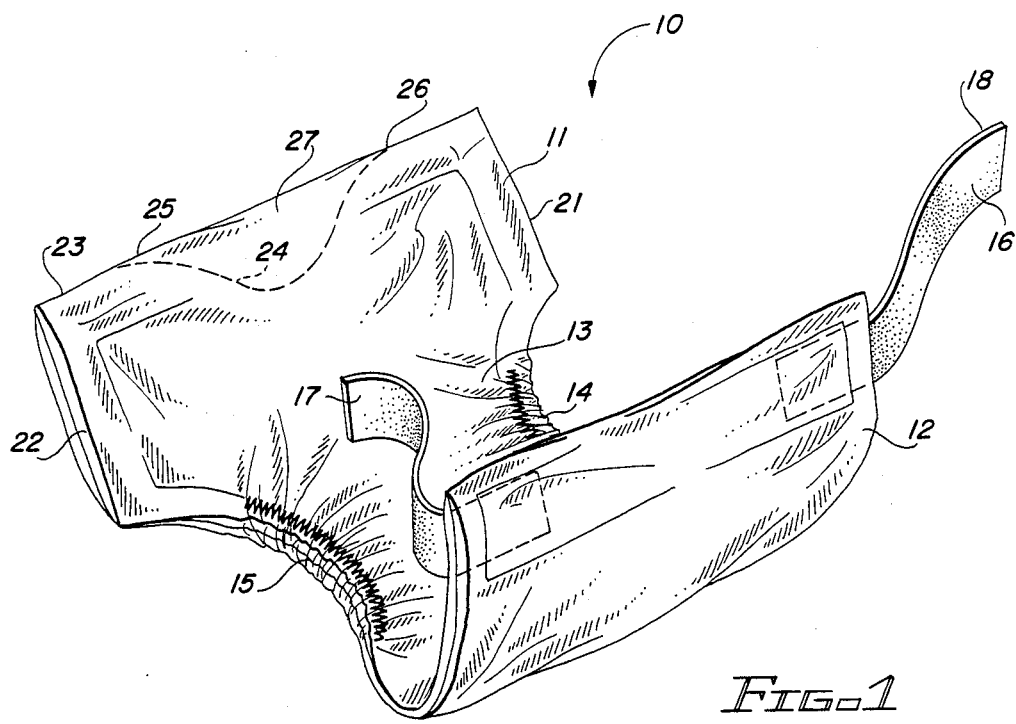
FIG. 1 is perspective view of a diaper in accordance with the present invention.
Figure 2:
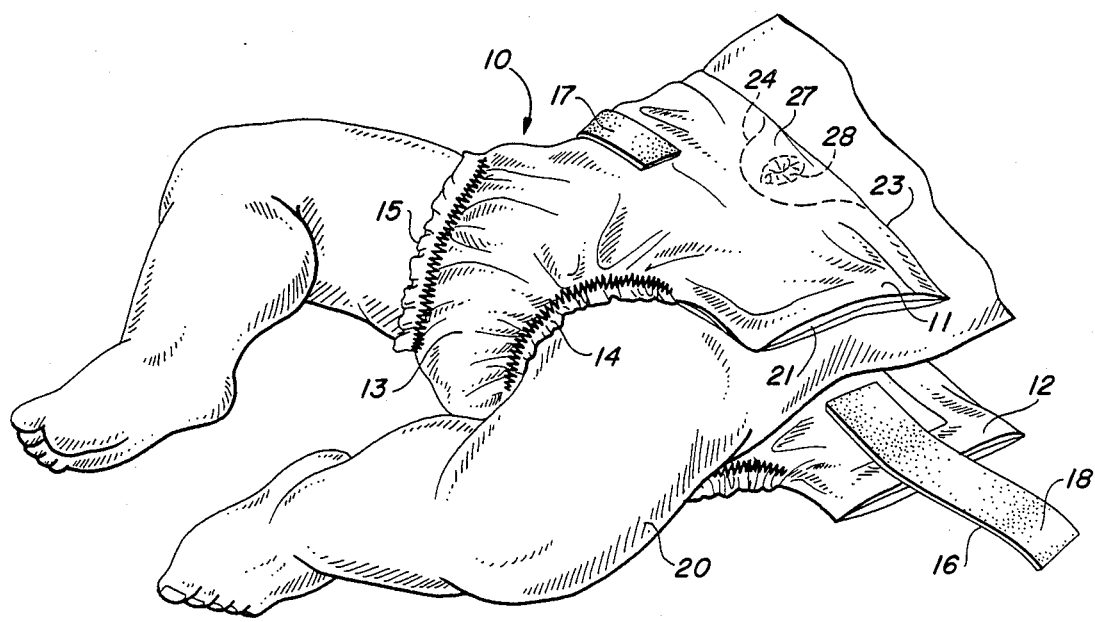
FIG. 2 is perspective view of a diaper in accordance with FIG. 1 placed on a baby.

Referring to the drawings and especially to FIGS. 1, 2 and 7 a disposable diaper 10 has a generally rectangular shape having a first end portion 11 and a second end portion 12 and a center portion 13. The center portion 13 has arcuate edges 14 and 15 shaped to fit around the babies legs in a manner to make the diaper 10 form fitting. The second end portion 12 has a pair of adhesive straps 16 and 17 attached thereto and having an adhesive or other attaching surface 18 on the end thereof so that the straps can be attached or taped to the first end portion 11 to hold the diaper of a baby 20 as shown in FIG. 2. The first end portion 11 has two side edges 21 and 22 and an edge 23 and a line of perforations 24 perforating the material and extend from a point 25 along the edge 23 to a point 26 along the edge 23 for removing a perforated area 27 removed along the edge 23. The perforated portion 27 is located along the middle of the edge 23 so that the removed portion is removed from over the baby's umbilical area or navel 28. Normally the perforated area would not be removed from most babies but is removed for young babies, during the first weeks after birth, when the umbilical area has not healed. The area tends to get infected from the urine and feces of the baby collecting in the diaper and especially from the urine which is soaking into the absorbent material of the diaper. Having the umbilical area 28 of the baby 20 open to air by tearing off the perforated section 27 allows the proper and rapid healing of the umbilical cord area and the proper formation of the navel.

FIGS. 3 through 6 shows alternate embodiments of the diapers shown in FIGS. 1 and 2. The diapers are each identical to that shown in 10 having a generally rectangular shape with a first end portion 11 a second end portion 12 and a middle portion 13. The middle portion 13 has removed portions 14 and 15 from each side. A pair of straps 16 and 17 are on each diaper in FIGS. 3 through 7 but each diaper differs in that the edge 23 has a different perforated line. Figure three has a triangular perforations 30 for removal of a triangular removal area 31. FIG. 4 has a square shaped perforation lines 32 for a removal of a square area 33. FIG. 5 has semi-circular arcuate perforations 34 for removing a semi-circular area 35 of the diaper. FIG. 6 has a different shaped curve performations 36 for removing a curved shape 37 from the diaper.

FIG. 7 illustrates a rear elevation of the diaper in which the adhesive straps 16 and 17 are attached to the back of the diaper which forms the edges 14 and 15 around the legs of the baby using the diaper.

It should be clear at this point that a disposable diaper has been provided with advantageously has a removable perforated area for removal in the case of young babies or in babies with infected umbilical or navel area to protect the baby from infection and to promote rapid healing of the area in new babies. However the present invention is not to be construed as limited to the form shown, which are to be considered illustrative rather than restrictive.

We claim:

1. A disposable diaper comprising:

Diaper means for placing on a baby and made of layered flat absorbent material having a generally rectangular shape and first and second end portions and a center portion, said center portion having arcuate edges extending into the generally rectangular shape to provide a form fitting diaper and said diaper means having a pair of attaching straps on said first and second ends for attaching said diaper means to a baby, the improvement comprising:

A removable perforated area in said first end portion along one edge thereof and positioned to fit over a navel area of a baby wearing said diaper means, said diaper means first end portion having an end edge and two side edges and said removable perforated area being positioned in the middle of the edge to form a removed portion from along the edge when said perforated area is removed, whereby said perforated area can be removed for young babies to prevent umbilical infection in said baby.

2. A disposable diaper in accordance with claim 1 in which said diaper means first end portion perforated portion is arcuate so as to form an arcuate end edge portion when said perforated portion is removed.

3. A disposable diaper in accordance with claim 1 in which said diaper means first end portion perforated portion is triangular so as to form a triangular end edge portion when said perforated portion is removed.

4. A disposable diaper in accordance with claim 1 in which said diaper means first end portion perforated portion is rectangular so as to form a rectangular end edge portion when said perforated portion is removed.

5. A disposable diaper in accordance with claim 1 in which said diaper means first end portion perforated portion is semi-circular so as to form a semi-circular end edge portion when said perforated portion is removed.

* * * * *